United States Patent [19]

Baker et al.

[11] Patent Number: 5,042,980
[45] Date of Patent: Aug. 27, 1991

[54] OPTICAL FIBER DIFFUSION TIP FOR UNIFORM ILLUMINATION

[75] Inventors: Glenn S. Baker, Wakefield; Edward L. Sinofsky, Peabody, both of Mass.

[73] Assignee: C. R. Bard, Inc., Murray Hill, N.J.

[21] Appl. No.: 358,443

[22] Filed: May 26, 1989

[51] Int. Cl.⁵ .............................................. A61B 17/36
[52] U.S. Cl. ........................................ 606/7; 606/192; 606/194; 604/96
[58] Field of Search ..................... 606/27-31, 606/1-3, 7, 13-17, 192, 194; 128/303.1, 395-398; 604/96

[56] References Cited

U.S. PATENT DOCUMENTS

| | | | |
|---|---|---|---|
| 3,641,332 | 2/1972 | Reick et al. | 240/1 EI |
| 4,195,907 | 4/1980 | Zamja et al. | 350/96.32 |
| 4,360,247 | 11/1982 | Beasley | 350/96.15 |
| 4,363,533 | 12/1982 | Stowe et al. | 350/96.33 |
| 4,387,954 | 6/1983 | Beasley | 350/96.15 |
| 4,403,826 | 9/1983 | Presby | 350/96.30 |
| 4,422,719 | 12/1983 | Orcutt | 350/96.30 |
| 4,466,697 | 8/1984 | Daniel | 350/96.30 |
| 4,470,407 | 9/1984 | Hussein | 128/6 |
| 4,512,762 | 4/1985 | Spears | 604/21 |
| 4,575,181 | 3/1986 | Ishikawa | 350/96.20 |
| 4,585,298 | 4/1986 | Mori | 350/96.10 |
| 4,625,724 | 12/1986 | Suzuki et al. | 128/398 X |
| 4,660,925 | 4/1987 | McCaughan, Jr. | 606/16 X |
| 4,676,231 | 6/1987 | Hisazumi et al. | 606/15 |
| 4,679,894 | 7/1987 | Pavlath | 350/96.15 |
| 4,693,244 | 9/1987 | Daikuzono | 128/398 X |
| 4,693,556 | 9/1987 | McCaughan, Jr. | 350/320 |
| 4,762,385 | 8/1988 | Fuse | 350/96.18 |
| 4,770,653 | 9/1988 | Shturman | 128/6 X |
| 4,784,133 | 11/1988 | Mackin | 606/7 |
| 4,799,479 | 1/1989 | Spears | 128/303.1 |
| 4,878,942 | 11/1989 | Sinofsky et al. | 128/395 |

FOREIGN PATENT DOCUMENTS 2154761 9/1985 United Kingdom .

OTHER PUBLICATIONS

Hiehle, Jr. et al., Am. J. Cardiology, vol. 56, Dec. 1, 1985, pp. 953-957.
Fujii et al, Optics and Laser Technology, Feb. 1984, pp. 40-44.

Primary Examiner—Robert A. Hafer
Assistant Examiner—Kerry Owen
Attorney, Agent, or Firm—Wolf, Greenfield & Sacks

[57] ABSTRACT

A diffusion tip coupled to the end of an optical fiber for directing laser energy outwardly in a cylindrical or other desired radiation pattern. The diffusion tip includes a core, a cladding around the core and a jacket around the cladding. The cladding has an index of refraction that is lower than that of the core and has a thickness selected to transmit a portion of the laser radiation that is carried through the optical fiber so that laser radiation penetrates through the cladding and the jacket over the length of the diffusion tip. The thickness of the cladding is about the same as or slightly less than the penetration depth of the evanescent field in the cladding. The cladding can be tapered along the length of the diffusion tip to provide a uniform radiation pattern. The diffusion tip is particularly useful in a laser balloon catheter utilized in coronary angioplasty.

14 Claims, 4 Drawing Sheets

OPTICAL FIBER DIFFUSION TIP FOR UNIFORM ILLUMINATION

FIELD OF THE INVENTION

This invention relates to optical fiber assemblies for transmission and diffusion of laser radiation and, more particularly, to an optical fiber diffusion tip for producing a substantially uniform cylindrical radiation pattern over a prescribed axial length. The diffusion tip is particularly useful in laser balloon catheters utilized in coronary angioplasty, but is not limited to such use.

BACKGROUND OF THE INVENTION

Balloon angioplasty has been utilized for a number of years to treat coronary arteries narrowed by plaque deposits. A catheter having an inflatable balloon secured to its distal end is advanced through an artery to a narrowed region. The balloon is then inflated with a fluid from an external source, causing the narrowed region of the artery to be expanded. The balloon is then deflated and withdrawn. A serious problem associated with balloon angioplasty has been the occurrence in up to 30% of the cases of so called restenosis, either immediately after the procedure or within six months. Immediate restenosis, also known as abrupt reclosure, results from flaps or segments of plaque and plaque-ridden tissue which are formed during balloon angioplasty and which can block the artery. Such blockage of the artery requires emergency surgery and often results in death. Furthermore, a surgical team is required to stand by during the balloon angioplasty procedure. Restenosis at a later time results from causes that are not totally known. Thrombus formation is believed to play an important part. Often repeat balloon angioplasty or surgery is required, and another episode of restenosis may occur.

A technique which has shown great promise for overcoming the problem of restenosis is the simultaneous application of heat and pressure to a plaque-narrowed region of the artery. The technique is described by John F. Hiehle, Jr. et al in "Nd-YAG Laser Fusion of Human Atheromatous Plaque Arterial Wall Separations in Vitro", *Am. J. Cardiology*, Vol. 56, Dec. 1, 1985, pages 953-957 and by J. Richard Spears in U.S. Pat. No. 4,799,479 issued Jan. 24, 1989. In accordance with this technique, a catheter having an inflatable balloon at its distal end is advanced to a narrowed region of an artery and the balloon is inflated, as in the case of balloon angioplasty. However, in distinction to balloon angioplasty, sufficient heat is applied through the wall of the balloon to fuse the surrounding tissue and thereby eliminate the flaps which can later block the artery One advantageous means of heating the surrounding tissue is by directing laser radiation through an optical fiber carried by the catheter and terminating within the balloon. The laser radiation is then directed through the balloon wall to cause heating of the surrounding tissue.

It has been found desirable to apply radiation which penetrates into the surrounding plaque and plaque ridden tissue and the artery wall and heats that region by radiant heating, in distinction to conductive heating by the balloon. Furthermore, it has been found desirable to apply such radiation at a power level of 20-40 watts for times on the order of about 20 seconds. In applying laser radiation at relatively high power levels, it is important to provide a relatively uniform cylindrical radiation pattern over the length of the balloon. Otherwise, hot spots can produce localized burning of tissue, and cold spots can leave potentially dangerous tissue flaps unfused.

Prior art techniques have been disclosed for directing laser radiation outwardly from the tip of an optical fiber. A tapered optical fiber surrounded with a diffusing medium for laser radiation treatment of tumors is disclosed in U.K Patent Application No. 2,154,761, published Sept. 11, 1985. An optical fiber surrounded with a scattering medium for producing a cylindrical pattern of light at the tip of an optical fiber is disclosed in U.S. Pat. No. 4,660,925, issued Apr. 28, 1987 to McCaughan, Jr. A technique for roughening the surface of an optical fiber tip to cause wide angle radiation of laser energy is disclosed by H. Fujii et al in "Light Scattering Properties of a Rough-Ended Optical Fiber", *Optics and Laser Technology*, February 1984, pages 40-44.

The aforementioned Spears U.S. Pat. No. 4,799,479, discloses an optical fiber that extends through a catheter and terminates in a light-disseminating tip located within an inflatable balloon. Spears teaches that the light-disseminating tip can be provided by removing the cladding from the fiber tip and roughening the fiber core surface. Spears also states that the light-disseminating tip can be made of an unspecified material which scatters laser energy.

U.S. Pat. No. 4,422,719 issued Dec. 27, 1983 to Orcutt discloses an optical illumination system including a transparent core surrounded by an unbonded sleeve. The surface of the core can have cuts or discontinuities to deflect light through the sleeve. In other embodiments, light is deflected through the sleeve by air bubbles in the core or by reflective particles embedded in the material of the sleeve.

U.S. Pat. No. 4,585,298 issued Apr. 29, 1986 to Mori discloses a photoradiator that is coupled to the end of an optical fiber. The photoradiator includes a transparent, light conducting member having a plurality of annular light-radiating strips on its outer surface. The strips have a higher refractive index than the light conducting portion so that light is coupled out of the photoradiator at the high refractive index strips. U.S. Pat. No. 4,195,907 issued Apr. 1, 1980 Zamja et al discloses the use of bubble-containing fibers. U.S. Pat. No. 4,466,697 issued Aug. 21, 1984 to Daniel discloses fibers having light-scattering particles in the core. The Zamja et al and Daniel patents illustrate techniques for emitting light from the sidewall of an optical fiber by providing scattering centers in the core of the optical fiber.

U.S. Pat. No. 4,363,533 issued Dec. 14, 1982 to Stowe et al discloses a fiber optic device which can be utilized as an acoustic transducer. The transducer comprises an optical fiber having an intermediate cladding between an inner core and an outer core. The intermediate cladding has an index of refraction lower than that of the inner core. Light is coupled from the inner core to the outer core as a result of penetration of the evanescent field through the cladding. The coupling between cores varies in response to mechanical pressure applied to the device. U.S. Pat. No. 4,679,894 issued July 14, 1987 to Pavlath discloses a fiber optic coupler wherein light is coupled between adjacent fibers by evanescent field coupling.

All known prior art light-disseminating or light-diffusing optical fiber tips have one or more disadvantages, including a lack of flexibility or power handling capability, a tendency to break, a nonuniform radiation pattern and difficulties in fabrication.

It is a general object of the present invention to provide an improved optical fiber diffusion tip.

It is another object of the present invention to provide an optical fiber diffusion tip having a substantially uniform cylindrical radiation pattern.

It is a further object of the present invention to provide an improved laser balloon catheter.

It is yet another object of the present invention to provide an optical fiber diffusion tip that is small in diameter and highly flexible.

It is still another object of the present invention to provide an optical fiber diffusion tip capable of delivering high power laser radiation.

It is another object of the present invention to provide a laser balloon catheter which produces substantially uniform heating of tissue surrounding the balloon.

SUMMARY OF THE INVENTION

According to the present invention, these and other objects and advantages are achieved in a laser transmission and diffusion assembly comprising an optical fiber having one end adapted for coupling to a source of laser radiation, and a tip assembly connected to the other end of the optical fiber for directing laser radiation outwardly in a generally radial direction. The tip assembly includes a core, a cladding around the core and a jacket around the cladding. The jacket has an index of refraction that is higher than that of both the core and the cladding. The cladding has an index of refraction that is lower than that of the core and has a thickness selected to transmit a portion of the laser radiation that is carried through the optical fiber, such that laser radiation penetrates through the cladding and the jacket over the length of the tip assembly.

A cladding with an index of refraction lower than that of the core reflects laser radiation back to the core when the angle of incidence of the radiation is less than the numerical aperture of the fiber. The tip assembly of the present invention operates by providing a cladding having a thickness that is about the same as or slightly less than the penetration depth of the evanescent field in the cladding. At each axial location along the tip assembly, a portion of the laser radiation is coupled from the core through the cladding and into the jacket. As a result, light is emitted generally radially along the length of the tip assembly. The amount of laser radiation that is coupled through the cladding is a function of the difference between the index of refraction of the core and the index of refraction of the cladding, the thickness of the cladding, the wavelength of the laser radiation being transmitted, the index of refraction of the jacket and the bending of the tip assembly. In a preferred embodiment, the cladding has a thickness of about one micrometer for a wavelength of 1.06 micrometers. The thickness of the cladding can be varied along the length of the tip assembly to provide a desired radiation pattern. In particular, the thickness of the cladding can be tapered along the length of the tip assembly to provide a substantially uniform cylindrical radiation pattern.

According to another aspect of the present invention, there is provided a laser balloon catheter comprising an elongated, flexible tube having a distal end and a proximal end, an inflatable balloon secured to the flexible tube at or near the distal end thereof, means for inflating and deflating the balloon, an optical fiber for carrying laser radiation through the flexible tube into the balloon, and tip assembly means located within the balloon and coupled to the optical fiber for directing laser radiation outwardly through a major portion of the balloon surface. The tip assembly means includes a core, a cladding around the core, and a jacket around the cladding. The cladding has an index of refraction that is lower than that of the core and has a thickness selected to transmit at least a portion of the laser radiation which penetrates from the core into the cladding. The jacket has an index of refraction that is higher than that of the core and the cladding, such that laser radiation carried through the optical fiber penetrates through the cladding and the jacket over the length of the tip assembly means.

BRIEF DESCRIPTION OF THE DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figure 1:
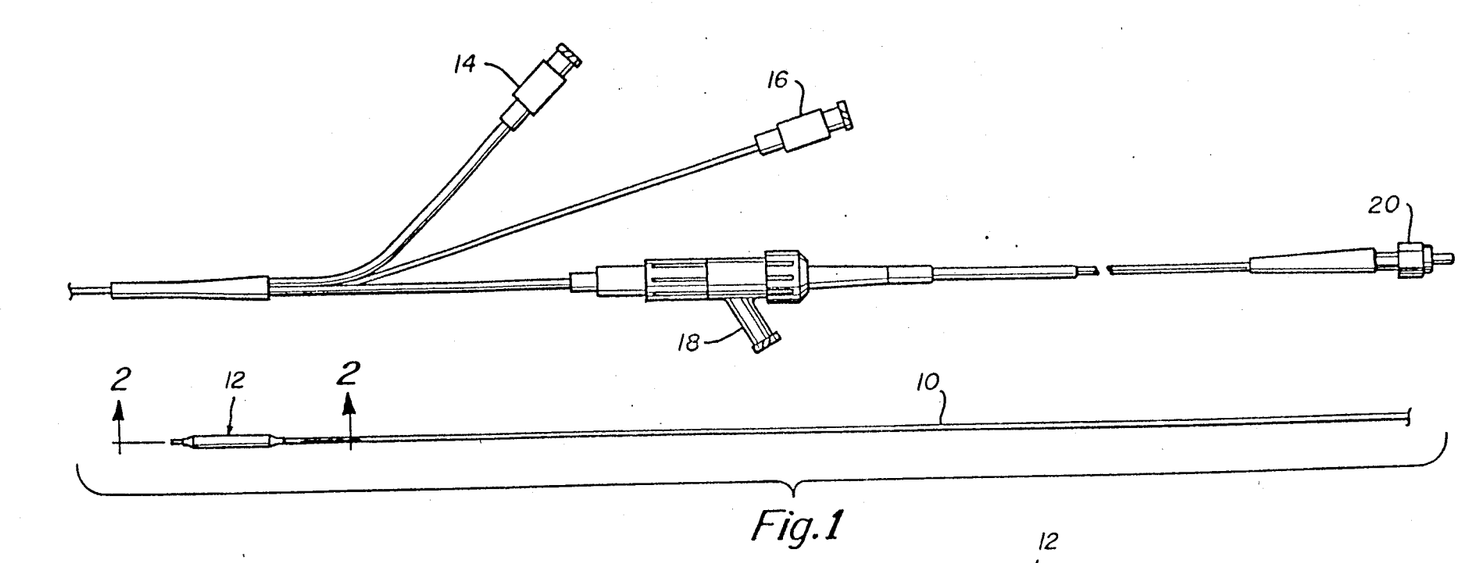
FIG. 1 is a fragmented illustration of a laser balloon catheter incorporating an optical fiber diffusion tip in accordance with the present invention.
Figure 2:
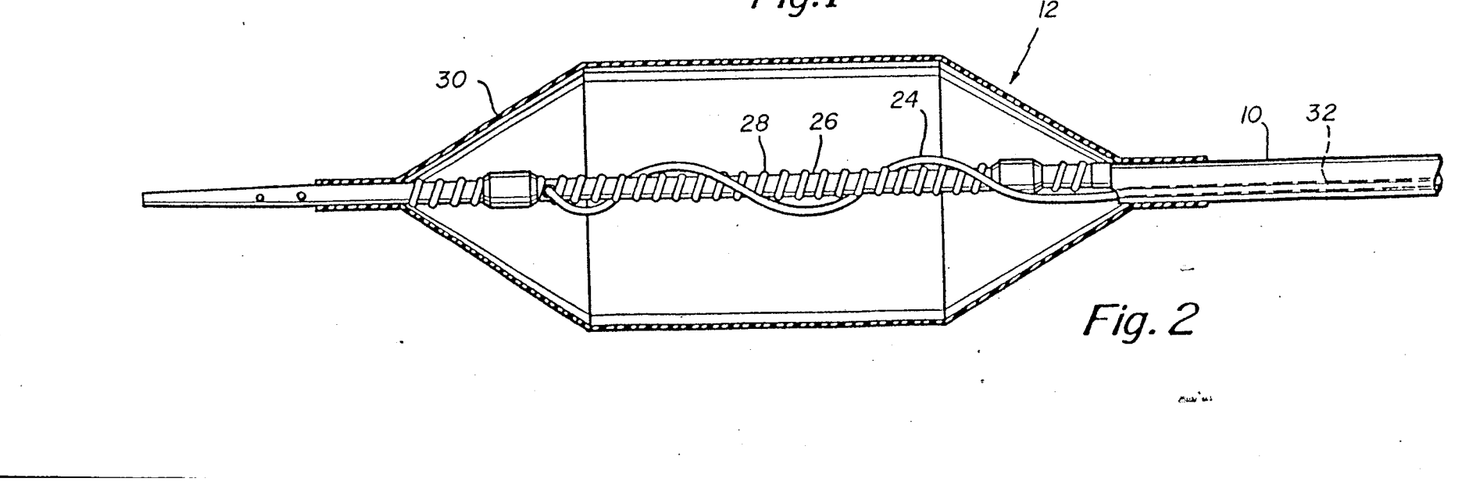
FIG. 2 is an enlarged cross-sectional view of the distal end of the laser balloon catheter taken along the lines 2—2 of FIG. 1.

A laser balloon catheter is shown in FIGS. 1 and 2. An elongated, flexible tube 10 has a laser balloon assembly 12 at its distal end and connectors 14, 16, 18 and 20 at its proximal end. The laser balloon assembly 12 includes an optical fiber tip assembly 24 (FIG. 2) for emitting laser radiation, a central shaft 26 adapted for carrying a guidewire (not shown) and for carrying a fluid to the treatment region, and a balloon 30 which is inflated and deflated from the proximal end of the flexible tube 10. The central shaft 26 includes a reinforcing spring 28 which prevents the shaft 26 from collapsing on the guidewire when balloon 30 is inflated. In a preferred embodiment, the flexible tube 10 includes three lumens for carrying an optical fiber, a guidewire and a inflation fluid.

An optical fiber 32 extends from connector 20 through the flexible tube 10 and terminates in optical fiber tip assembly 24. Connector 20 is coupled to the output of a laser source (not shown). A guidewire is introduced into the catheter through connector 16 and passes through flexible tube 10 and through central shaft 26. A source of pressurized fluid (not shown) is coupled through connector 14 to the interior of balloon 30. Means for evacuating the balloon are also coupled through connector 14 to the interior of balloon 30.

The purpose of the optical fiber tip assembly 24 is to direct laser energy outwardly through the wall of balloon 30 with a desired radiation pattern, typically a generally uniform cylindrical pattern. In the embodiment of FIG. 2, the optical fiber tip assembly 24 is spirally configured around central shaft 26 to limit shadowing by central shaft 26. Further details regarding the construction of a laser balloon catheter are provided in pending application Ser. No. 106,609, filed Oct. 8, 1987 and in the aforementioned U.S. Pat. No. 4,799,479, which are hereby incorporated by reference.

Figure 3:
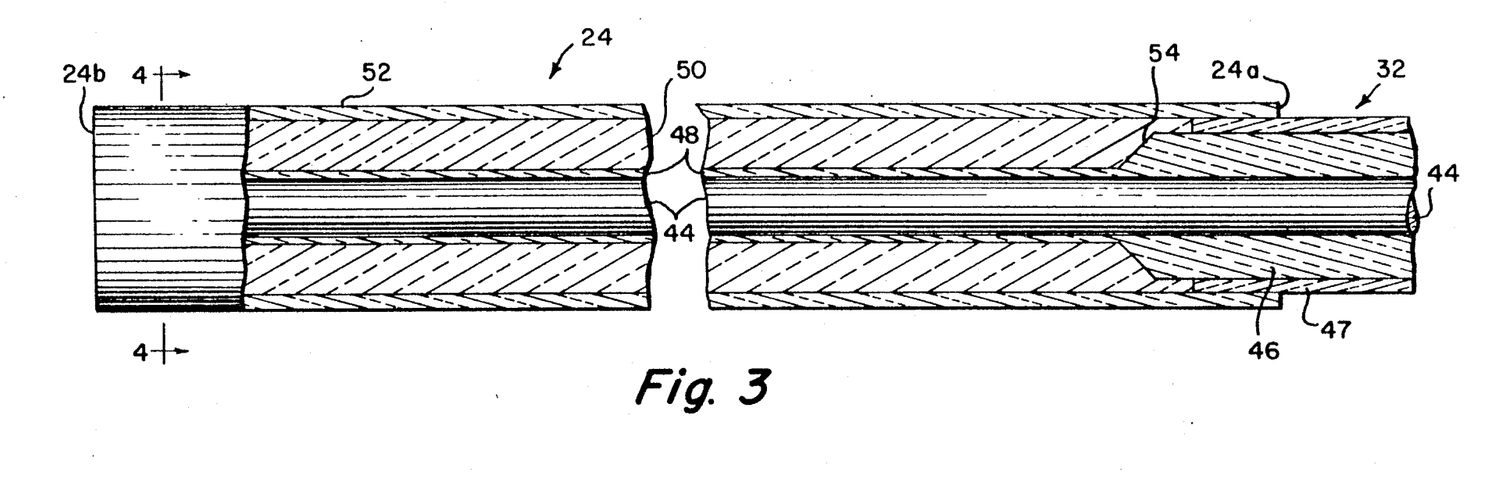
FIG. 3 is an enlarged cross-sectional view of an optical fiber diffusion tip in accordance with the present invention.
Figure 4:
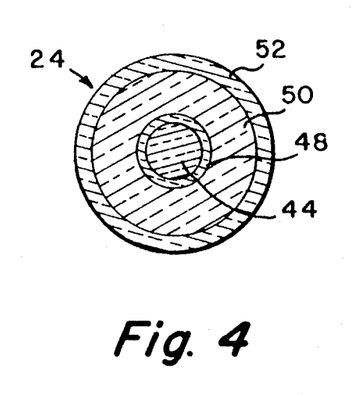
FIG. 4 is an enlarged cross-sectional view of the optical fiber diffusion tip taken along the lines 4—4 of FIG. 3.

The optical fiber tip assembly 24 in accordance with the present invention is shown in FIGS. 3 and 4, which are enlarged and not to scale for ease of understanding. The tip assembly 24 is coupled to the distal end of optical fiber 32. The optical fiber 32 includes a core 44, a cladding 46 and a buffer 47. The tip assembly, or diffusion tip 24, includes an extension of core 44, a thin cladding 48 and a jacket 50. In the embodiment of FIGS. 3 and 4, the diffusion tip 24 includes an optional heat-formable tube 52 for providing the spiral configuration, as described hereinafter. The cladding 48 has an index of refraction that is lower than the index of refraction of core 44. Jacket 50 has an index of refraction that is higher than the indices of refraction of both the core 44 and the cladding 48. As described hereinafter, the parameters of the cladding 48 are selected relative to core 44 to emit laser radiation in a cylindrical or other desired pattern over the length of diffusion tip 24. The jacket 50 protects core 44 and cladding 48 from damage without substantial attenuation of laser radiation that passes through cladding 48.

The optical fiber 32 is a conventional multimode optical fiber including core 44 surrounded by relatively thick cladding 46 having a refractive index lower than that of the core 44. Laser radiation incident on the interface between core 44 and cladding 46 at less than the critical angle penetrates partway into cladding 46, is reflected back into the core and is guided through the fiber in conventional fashion. The incident laser radiation penetrates into the cladding by a predetermined penetration depth. The portion of the laser radiation which penetrates into the cladding is known as an evanescent wave or evanescent field. The penetration depth is a function of the difference in refractive indices of the core and the cladding, the wavelength of the laser radiation and the bending of the fiber. The penetration depth is also a function of the angle incidence of the laser radiation on the core-cladding interface. However, in an optical fiber, the angle of incidence is limited by the geometry of the fiber. In a conventional optical fiber such as fiber 32, the cladding 46 is substantially thicker than the penetration depth of the evanescent field, and no laser radiation penetrates through the sidewall of the fiber.

Figure 5A:
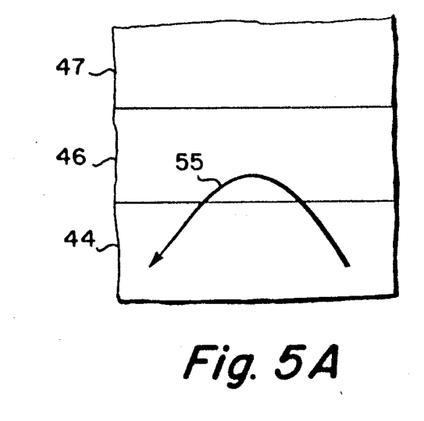
FIG. 5A is an enlarged, partial cross-sectional view of a conventional optical fiber showing penetration of laser radiation into the cladding.
Figure 5B:
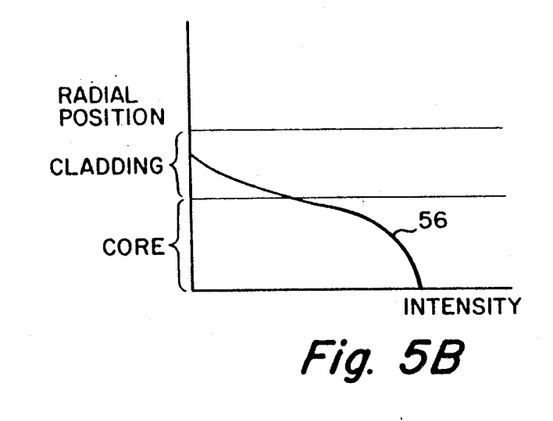
FIG. 5B is a graphic representation of laser intensity as a function of radial position in the conventional optical fiber of FIG. 5A.

The operation of a conventional optical fiber is illustrated in FIGS. 5A and 5B. In FIG. 5A, laser energy 55 that is incident on the interface between core 44 and cladding 46 penetrates partway into cladding 46 and is reflected back into core 44. Since the cladding 46 is substantially thicker than the penetration depth of the evanescent field, no laser energy is transmitted through cladding 46. The distribution of laser intensity as a function of radial position in the optical fiber of FIG. 5A is shown in FIG. 5B. The distribution is a generally bell shaped curve 56 with a maximum at the center of the core. The intensity falls to zero within the cladding, and no laser energy is transmitted through the cladding.

The diffusion tip 24 in accordance with the present invention takes advantage of the evanescent field to produce light dissemination or diffusion. The cladding 48 has a thickness that is about the same as or slightly less than the penetration depth of the evanescent field. As indicated above, the cladding 48 has a lower refractive index than the core 44, and the jacket 50 has a refractive index that is higher than the refractive indices of both the core 44 and the cladding 48. Since the cladding 48 has a lower refractive index than core 44, laser radiation is reflected by cladding 48.

Figure 5C:
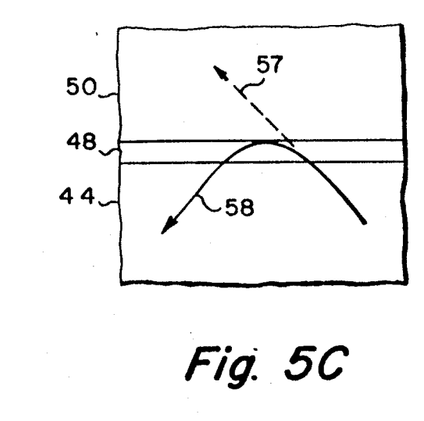
FIG. 5C is an enlarged, partial cross-sectional view of the diffusion tip of the invention showing penetration of laser radiation through the cladding.

The operation of diffusion tip 24 is illustrated pictorially in FIG. 5C. Since the cladding 48 has a thickness that is about the same as or slightly less than the penetration depth of the evanescent field, a portion 57 of the laser radiation is transmitted through the cladding 48 and through the jacket 50 rather than being reflected. A portion 58 of the laser radiation which is not transmitted through the cladding 48 is reflected into core 44 and continues down the diffusion tip 24 toward its distal end. At each location along diffusion tip 24, a portion 57 of the laser radiation is transmitted through cladding 48, and a portion 58 is reflected. As a result, laser radiation is emitted along the entire length of diffusion tip 24. For a given laser radiation wavelength, the thickness and index of refraction of cladding 48 can be selected to produce a cylindrical or other desired radiation pattern.

Figure 5D:
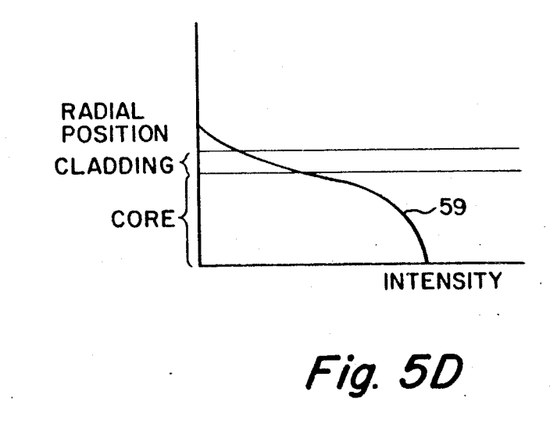
FIG. 5D is a graphic representation of laser intensity as a function of radial position in the diffusion tip of FIG. 5C.

The distribution of laser intensity as a function of radial position in the diffusion tip 24 is illustrated in FIG. 5D as curve 59. A portion of the curve 59 radially outside the cladding is emitted from the diffusion tip.

In a preferred embodiment, the core 44 and the cladding 48 of the diffusion tip 24 are integral extensions of the optical fiber 32. The desired thickness of cladding 48 can be obtained by etching the tip of optical fiber 32 using hydrofluoric acid as an etchant. The core 44 and cladding 48 are typically fused silica having the required indices of refraction. The jacket 50 can be any material which adheres to the cladding 48 and which has the required index of refraction. A preferred jacket material is an optically transparent epoxy.

Other techniques can be utilized to fabricate the thin cladding 48. The conventional cladding can be entirely removed from the optical fiber in the tip region, and the core can be dipped in a suitable low index of refraction material. In another approach, the fiber can be heated and drawn to provide the desired cladding thickness. In still other approaches, the cladding 48 can be formed by vapor deposition or ion bombardment.

As indicated above, the penetration depth of the evanescent field into the cladding surrounding core 44 is a function of laser wavelength, the indices of refraction of the core and the cladding and any bending to which the diffusion tip 24 is subjected. The penetration depth, also known as the Goos-Haenchen shift, can be expressed as:

$$d = \lambda/2\pi \, (n_1^2 \sin^2 \theta - n_2^2)^{\frac{1}{2}}]$$

where
- d = penetration depth
- λ = wavelength of laser radiation
- $n_1$ = index of refraction of core
- $n_2$ = index of refraction of cladding
- θ = angle of incidence In most cases, a cylindrical radiation pattern which is substantially uniform along the length of diffusion tip 24 and which is circumferentially uniform is desired. It has been found that when cladding 48 is uniform in thickness along the length of diffusion tip 24, the laser intensity is somewhat nonuniform along the length of diffusion tip 24. In order to provide better uniformity, the thickness of cladding 48 can be varied along the length of diffusion tip 24. In particular, the cladding can be tapered from thicker at the proximal end 24a of diffusion tip 24 where it connects to optical fiber 32 to thinner at the distal end 24b thereof. The gradual reduction in the thickness of cladding 48 produces a more uniform pattern. In other cases, it may be desirable to produce a radiation pattern that is nonuniform along the length of diffusion tip 24. In this case, the thickness of cladding 48 can be controlled to produce the desired radiation pattern. A variable thickness cladding 48 can be obtained by removing the tip assembly from the etching solution at a controlled rate so that different parts of the cladding are immersed in the etching solution for different times.

For a cladding 48 of constant thickness, a fixed percentage of the laser energy is coupled out of the core per unit length. Since the laser energy is gradually being coupled out of the fiber, fixed percentage coupling produces a decrease in the emitted intensity over the length of the diffusion tip. To obtain constant intensity per unit length, a variable coupling percentage is utilized. Variable coupling percentage can be accomplished by tapering the thickness of the cladding. Variable coupling percentage can also be accomplished by variable bending of the fiber. In the embodiment of FIGS. 1 and 2 where the diffusion tip 24 has a spiral or helical configuration, the pitch of the helix can be varied.

In a preferred embodiment, the diffusion tip 24 is used at a wavelength of 1.06 micrometers and has a length of about 2-3 centimeters. In the preferred embodiment, the core 44 has a diameter of 105 micrometers, an index of refraction of 1.45 and is fabricated of pure fused silica. The cladding 48 has a thickness of about 1 micrometer (resulting in an outside diameter of 107 micrometers), an index of refraction of 1.43 and is fabricated of fluorine doped fused silica. In a most preferred embodiment, the cladding 48 is tapered in thickness from about one micrometer at the proximal end 24a of diffusion tip 24 to approximately zero thickness at the distal end 24b thereof. This corresponds to an outside diameter of 107 micrometers at the proximal end and an outside diameter of 105 micrometers at the distal end. In the preferred embodiment, the core 44 of the diffusion tip 24 is an integral extension of the core of optical fiber 32, and cladding 48 is an integral extension of optical fiber cladding 46. The cladding 46 has an outside diameter of 125 micrometers, and the tapered transition 54 between cladding 46 and cladding 48 preferably occurs over an axial distance of about one quarter millimeter. The jacket 50 is a clear epoxy available from Masterbond and having an index of refraction of greater than 1.5. The jacket 50 can be formed by dipping the fiber in epoxy to form a thin coating which protects the fiber surface and maintains strength.

In the embodiment of FIGS. 1-4, the diffusion tip 24 is utilized in a heat-formable tube 52 to provide a spiral configuration. In a preferred embodiment, the tube 52 is polyethylene terephthalate (PET) having an outside diameter of 0.014-inch and an inside diameter of 0.008-inch. The epoxy jacket 50 fills the space between cladding 48 and tube 52. The PET tube is preformed into a desired spiral configuration by wrapping it around a mandrel and heat treating it. The mandrel has an outside diameter of 0.026-inch and provides two turns over a length of 20 millimeters. Then core 44 and cladding 48, protected by a thin coating of epoxy as described above, are inserted into tube 52, and epoxy is injected between them. Curing of the epoxy produces a unitary diffusion tip assembly. Further details regarding fabrication of the spiral configuration are provided in the aforementioned application Ser. No. 106,609.

The bending of the spiral diffusion tip assists in its operation. Laser energy is launched into the fiber 32 with a low numerical aperture (0.1-0.15) in order to excite only low order modes, thereby providing the catheter with good transmission and low bending losses. At the diffusing tip 24, the bending of the fiber causes low order modes to be coupled to high order modes. The higher order modes are more lossy and travel closer to the cladding. For evanescent coupling to occur, the laser energy must be traveling close to the cladding. Low order modes that do not couple to high order modes are transmitted out the distal end of the fiber.

In other embodiments, the diffusion tip can be epoxied to the outer surface of central shaft 26 in a spiral or straight configuration with tube 52 omitted. The tube 52 is used as one way to effect preforming of the diffusion tip and may be omitted when preforming is not required. In a straight configuration, uniform light distribution can be achieved by the use of a transverse waveguide surrounding both the diffusion tip and the central shaft 26 as shown and described in application Ser. No. 106,609. The mounting of the diffusion tip of the present invention in the balloon assembly is a matter of choice. However, any bending of core 44 and cladding 48 must be taken into account in determining thickness of cladding 48, since the evanescent field penetrates into the cladding to a greater depth when the diffusion tip 24 is bent, for example, into a spiral configuration.

Typical radiation patterns for various diffusion tip configurations are shown in FIGS. 6A-6D. In each case, relative laser intensity emitted by the diffusion tip is plotted as a function of axial position along the diffusion tip. Also, in each case the proximal end of the diffusion tip is designated by the numeral 60, and the distal end is designated by the reference numeral 62. Furthermore, in each case, an optical fiber having a spiral configuration as described above and having a core with a 105 micrometer diameter was utilized.

Figure 6A:
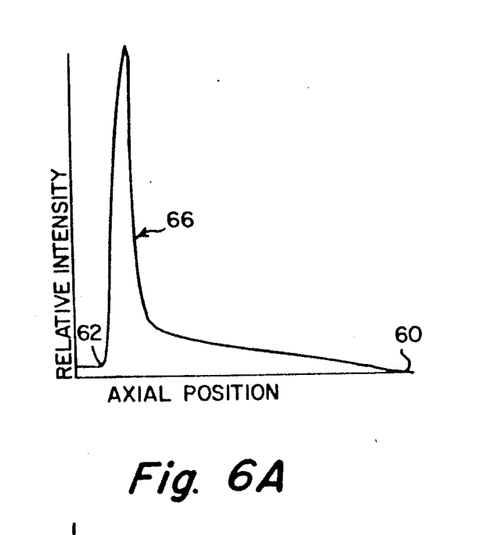
FIGS. 6A-6D are graphic representations of relative laser intensity as a function of axial position along the diffusion tip for different cladding configurations.

In FIG. 6A, the cladding 48 was uniform in thickness over the length of the diffusion tip and had an outside diameter of 109 micrometers (2 micrometer thickness). As indicated by curve 66, most of the laser radiation is emitted near the distal end of the diffusion tip.

Figure 6B:
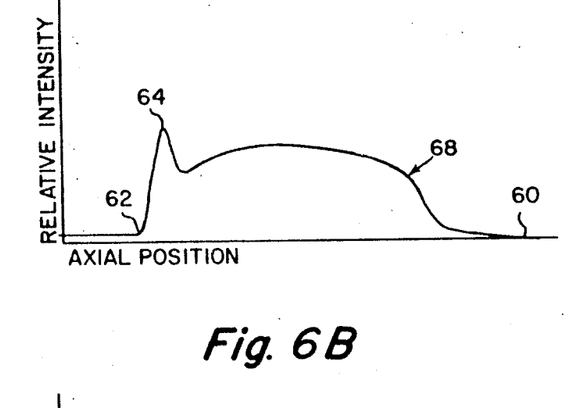

In FIG. 6B, the cladding 48 was uniform in thickness over the length of the diffusion tip and had an outside diameter of 107 micrometers (1 micrometer thickness). The laser radiation pattern indicated by curve 68 is considerably more uniform than the pattern shown in FIG. 6A. However, a peak 64 appears near the distal end.

Figure 6C:
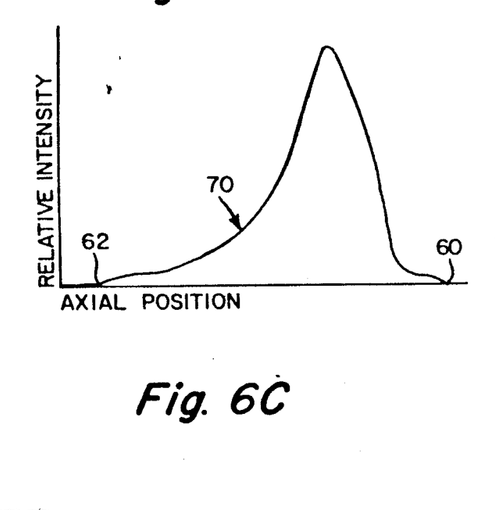

In FIG. 6C, all cladding was removed from the diffusion tip, producing an outside diameter of 105 micrometers. As indicated by curve 70, most of the laser radiation is emitted near the proximal end of the diffusion tip.

Figure 6D:
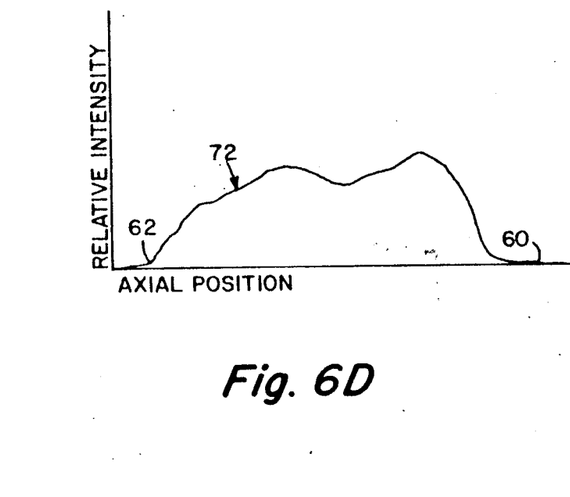

In FIG. 6D, the cladding 48 is tapered from 107 micrometers outside diameter (1 micrometer thickness) at the proximal end of the diffusion tip to 105 micrometers outside diameter (zero thickness) at the distal end of the diffusion tip. As indicated by curve 72, the pattern is fairly uniform and the peak near the distal end has been eliminated.

The diffusion tip 24 is designed for a desired radiation pattern at a selected wavelength. In the present example, the design wavelength is 1.06 micrometers. All light having wavelengths shorter than the design wavelength is guided more distally in the diffusion tip, thus producing a distribution similar to that shown in FIG. 6A. All light having wavelengths longer than the design wavelength is guided more proximally in the diffusion tip, thus producing a distribution similar to that shown in FIG. 6C. Furthermore, the radial collection efficiency of the diffusion tip is wavelength-dependent. The radial collection efficiency measures the ability of the diffusing tip to direct light energy in a reverse direction through optical fiber 32. All light having wavelengths shorter than the design wavelength can be collected over the total length of the diffusion tip. All light having wavelengths longer than the design wavelength is collected over a fraction of the diffusion tip length.

The diffusion tip of the present invention is small in diameter and flexible. In addition, the diffusion tip is resistant to breakage. The radiation pattern can be controlled by appropriate selection of cladding thickness and taper.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A laser balloon catheter comprising:
   an elongated, flexible tube having a distal end and a proximal end;
   an inflatable balloon secured to said flexible tube at or near the distal end thereof;
   means for inflating and deflating said balloon;
   an optical fiber for carrying laser radiation through said flexible tube into said balloon; and
   tip assembly means located within said balloon and coupled to said optical fiber for directing laser radiation outwardly through a major portion of the balloon surface, said tip assembly means including a core, a cladding around the core and a jacket around the cladding, said cladding having an index of refraction lower than that of the core and having a thickness selected to transmit outwardly through the cladding and the jacket at least a portion of the laser radiation carried through said optical fiber.

2. A laser balloon catheter as defined in claim 1 wherein the thickness of said cladding is selected to provide a substantially uniform axial distribution of laser radiation over the length of said tip assembly means.

3. A laser balloon catheter as defined in claim 1 wherein the thickness of said cladding is varied over the length of said tip assembly means to provide a desired axial distribution pattern.

4. A laser balloon catheter as defined in claim 1 wherein said cladding is tapered from thicker at the proximal end to thinner at the distal end.

5. A laser balloon catheter as defined in claim 1 wherein said cladding has a thickness of about one micrometer for a laser wavelength of about 1.06 micrometers.

6. A laser balloon catheter as defined in claim 1 wherein said core and said cladding comprise fused silica and said jacket comprises epoxy.

7. A laser balloon catheter as defined in claim 1 wherein the core of said tip assembly means is integral with the core of said optical fiber.

8. A laser balloon catheter as defined in claim 1 wherein said cladding is varied in thickness over the length of said tip assembly means to provide a substantially uniform axial distribution pattern.

9. A laser balloon catheter as defined in claim 1 wherein said tip assembly means further includes a heat formable tube around said jacket for forming said tip assembly means into a desired shape.

10. A laser balloon catheter as defined in claim 9 further including central shaft means located within said balloon, said tip assembly means being located between said central shaft means and the balloon surface.

11. A laser balloon catheter as defined in claim 1 wherein said core, said cladding and said jacket have a predetermined bend selected to cause transmission of laser radiation through said cladding.

12. A laser balloon catheter comprising:
    an elongated, flexible tube having a distal end and a proximal end;
    an inflatable balloon secured to said flexible tube at or near the distal end thereof;
    means for inflating and deflating said balloon;
    an optical fiber for carrying laser radiation through said flexible tube into said balloon; and
    tip assembly means located within said balloon and coupled to said optical fiber for directing laser radiation outwardly through a major portion of the balloon surface, said tip assembly means including a core, a cladding around the core and a jacket around the cladding, said cladding having an index of refraction lower than that of the core and having a thickness selected to transmit at least a portion of the laser radiation which penetrates from said core into said cladding, said jacket having an index of refraction higher than that of said core and said cladding such that laser radiation carried through said optical fiber penetrates through said cladding and said jacket over the length of said tip assembly means.

13. A laser balloon catheter comprising:
    an elongated, flexible tube having a distal end and a proximal end;
    an inflatable balloon secured to said flexible tube at or near the distal end thereof;
    means for inflating and deflating said balloon;
    an optical fiber for carrying laser radiation through said flexible tube into said balloon; and
    tip assembly means located within said balloon and coupled to said optical fiber for directing laser radiation outwardly through a major portion of the balloon surface, said tip assembly means including a core, a cladding around the core and a jacket around the cladding, said cladding having a thickness selected to transmit outwardly through the cladding and the jacket a first portion of the laser radiation and to reflect a second portion of the laser radiation that is carried through said optical fiber, such that laser radiation penetrates through said cladding and said jacket over at least a portion of the length of said tip assembly means.

14. A laser balloon catheter comprising:

an elongated, flexible tube having a distal end and a proximal end;

an inflatable balloon secured to said flexible tube at or near the distal end thereof;

an optical fiber for carrying laser radiation through said flexible tube into said balloon; and a tip assembly located within said balloon and connected to said optical fiber for directing laser radiation through said balloon, said tip assembly comprising a length of optical fiber including a core, a cladding around the core and a jacket around the cladding, said cladding having a thickness selected to transmit laser radiation outwardly through the cladding and the jacket such that laser radiation is directed through substantially the entire circumference of the balloon simultaneously.

* * * * *